(12) United States Patent
Sherman

(10) Patent No.: US 8,591,514 B2
(45) Date of Patent: Nov. 26, 2013

(54) RETROGRADE CUTTER WITH ROTATING BLADE

(75) Inventor: Gary Scott Sherman, Naples, FL (US)

(73) Assignee: Arthrex, Inc., Naples, FL (US)

( * ) Notice: Subject to any disclaimer, the term of this patent is extended or adjusted under 35 U.S.C. 154(b) by 538 days.

(21) Appl. No.: 12/647,254

(22) Filed: Dec. 24, 2009

(65) Prior Publication Data

US 2010/0168750 A1    Jul. 1, 2010

Related U.S. Application Data

(63) Continuation-in-part of application No. 12/114,599, filed on May 2, 2008.

(60) Provisional application No. 61/141,183, filed on Dec. 29, 2008, provisional application No. 60/915,607, filed on May 2, 2007.

(51) Int. Cl.
*A61B 17/56* (2006.01)

(52) U.S. Cl.
USPC .......................................... 606/80; 606/86 R

(58) Field of Classification Search
USPC ............ 606/84, 96, 102, 79–80, 86 R, 83, 606/174–175, 167, 170; 623/13.11–13.2; 403/84–85, 91–94, 98, 101
See application file for complete search history.

(56) References Cited

U.S. PATENT DOCUMENTS

| | | | |
|---|---|---|---|
| 5,147,373 A | 9/1992 | Ferzli | |
| 5,649,947 A | 7/1997 | Auerbach et al. | |
| 7,918,784 B2 * | 4/2011 | Wellborn et al. | 600/104 |
| 2003/0135218 A1 | 7/2003 | Eckman | |
| 2004/0106940 A1 * | 6/2004 | Shaolian et al. | 606/170 |
| 2004/0199166 A1 * | 10/2004 | Schmieding et al. | 606/79 |
| 2005/0240193 A1 | 10/2005 | Layne et al. | |
| 2006/0195112 A1 * | 8/2006 | Ek | 606/86 |
| 2007/0276391 A1 * | 11/2007 | Graves et al. | 606/80 |
| 2007/0276395 A1 * | 11/2007 | Burn | 606/80 |
| 2008/0249481 A1 | 10/2008 | Crainich et al. | |
| 2008/0306483 A1 | 12/2008 | Iannarone | |
| 2009/0275950 A1 | 11/2009 | Sterrett et al. | |

FOREIGN PATENT DOCUMENTS

| | | | |
|---|---|---|---|
| EP | 1 690 499 A2 | 8/2006 | |
| EP | 1 987 786 | 11/2008 | |
| WO | WO 9618346 A1 * | 6/1996 | A61B 17/32 |

* cited by examiner

*Primary Examiner* — Nicholas Woodall
*Assistant Examiner* — Larry E. Waggle, Jr.
(74) *Attorney, Agent, or Firm* — Dickstein Shapiro LLP

(57) ABSTRACT

A cutting instrument having a body, a blade at a distal end of the body, and a mechanism for rotating the blade from a first to a second position. The instrument can be used in a method of retrograde drilling a hole in bone. The cutting instrument is provided with a mechanism (for example, a pin and a slot) that converts linear motion into rotational motion and locks the blade into position. The cutting blade is configured to engage the shaft of the instrument and to lock into the shaft. The cutting blade is articulated between at least a first "straight" position (for example, about parallel to the longitudinal axis of the instrument) when the instrument cuts in an antegrade manner, and at least a second "flip" position (for example, a non-parallel position relative to the longitudinal axis of the instrument) when the instrument cuts in a retrograde manner. The cutting blade may be provided with a suture passing notch. The cutter instrument may also include a button mechanism for controlling the linear movement.

7 Claims, 5 Drawing Sheets

RETROGRADE CUTTER WITH ROTATING BLADE

CROSS-REFERENCE TO RELATED APPLICATIONS

This application claims the benefit of U.S. Provisional Application No. 61/141,183 entitled "MECHANISM FOR CONVERTING LINEAR MOVEMENT INTO ROTATIONAL MOVEMENT FOR SURGICAL INSTRUMENT," filed on Dec. 29, 2008, the entire disclosure of which is incorporated by reference herein. This application is also a continuation-in-part of U.S. application Ser. No. 12/114,599 (published as U.S. Publ. No. 2009/0275950 A1), filed May 2, 2008, which claims priority to U.S. Provisional Application No. 60/915,607, filed on May 2, 2007, the entire disclosures of which are hereby incorporated by reference.

FIELD OF THE INVENTION

The present invention relates to a mechanism for converting linear movement into rotational movement for a surgical instrument, such as a flip retrograde cutting instrument.

BACKGROUND OF THE INVENTION

During arthroscopic surgery, a small incision is made in the skin covering the arthroscopic site or joint, and a cannula is inserted in the incision to provide a pathway for surgical instruments to be placed in the joint and manipulated through arthroscopic visualization. Surgical instruments inserted through cannulas must be long and thin—this presents limitations on instruments for cutting tissue, as the diameter of the cannula ordinarily limits the width of the cutting implement.

Retrograde drilling of sockets and tunnels for ACL reconstruction using a flip cutter is known and described, for example, in U.S. application Ser. No. 12/114,599, filed on May 2, 2008, published as U.S. Publ. No. 2009/0275950 A1 and EP 1987786, the disclosures of which are incorporated by reference herein. This prior published application describes a flip retrograde cutter having a blade, preferably a flip blade, that is configured to articulate between at least a first "straight" position, for example, substantially parallel to a longitudinal axis of the flip retrograde cutter, and at least a second "flip" position, for example, a non-parallel position relative to the longitudinal axis of the flip retrograde cutter. Using such a flip retrograde cutter, a recipient site socket can be created from the inside out, i.e., using a retrograde technique, with minimal incisions of distal cortices and reduced intraarticular bone fragmentation of tunnel rims.

The flip retrograde cutter described above may be employed in a retrograde manner to form a recipient socket (to accommodate an osteochondral transplant, or to allow retrograde fixation of a graft within two sockets, for example). Formation of the recipient socket begins by inserting the flip retrograde cutter in the "straight" configuration into the joint space, preferably from the outside in, through a small diameter tunnel. A locking tube of the instrument is then retracted so that the blade can be articulated into the "flip" configuration, i.e., into a position other than the "straight" position and preferably at about 90 degrees to the longitudinal axis of the instrument. The device is locked in the "flip" position by tightening the locking tube. A socket is created by conducting a drilling operation, i.e., by rotating the instrument, while the device is pulled outwardly.

A need exists for a mechanism that facilitates flipping of the blade in the above-described instrument by converting linear movement of the shaft into rotational movement of the cutter blade (without the need to manually flip the cutter blade into position within the joint).

SUMMARY OF THE INVENTION

The present invention provides a cutting instrument that is designed to automatically convert linear movement of the shaft of the instrument into a rotational movement of the cutter tip (for example, a blade) of the instrument. The flip cutter instrument is provided with a mechanism (for example, a pin and a slot) that converts linear motion into rotational motion and locks the blade into position. The cutting blade is configured to engage the shaft of the instrument and to lock into the shaft. The cutting blade is articulated between at least a first "straight" position (for example, about parallel to the longitudinal axis of the instrument) when the instrument cuts in an antegrade manner, and at least a second "flip" position (for example, a non-parallel position relative to the longitudinal axis of the instrument) when the instrument cuts in a retrograde manner. The cutting blade may be provided with a suture passing notch. The cutter instrument may also include a button mechanism for controlling the linear movement.

The cutter of the present invention may be employed in an antegrade manner, or in a retrograde manner, or both in an antegrade and retrograde manner, to form a recipient socket (to accommodate an osteochondral transplant, or to allow retrograde fixation of a graft within two sockets, for example).

These and other features and advantages of the invention will be more apparent from the following detailed description that is provided in connection with the accompanying drawings and illustrated exemplary embodiments of the invention.

DETAILED DESCRIPTION

The following description is provided to enable any person skilled in the art to make and use the invention and sets forth the best modes contemplated by the inventors of carrying out their invention. Various modifications, however, will remain readily apparent to those skilled in the art.

The present invention provides a flip cutter instrument that is designed to automatically convert linear movement of the shaft of the instrument into a rotational movement of the cutter tip (blade) of the instrument. The flip cutter instrument is provided with a mechanism (such as a pin and a slot, for example) that converts linear motion into rotational motion and locks the blade into position. The cutting blade is configured to engage the shaft of the instrument and to lock into the shaft. The blade is articulated between at least a first "straight" position (for example, about parallel to the longitudinal axis of the instrument) and at least a second "flip" position (for example, a non-parallel position relative to the longitudinal axis of the instrument). The cutting blade may be provided with a suture passing notch.

The instrument may function in an antegrade or retrograde manner (when in the "flip" mode), or both in an antegrade or retrograde manner, to form a recipient socket (to accommodate an osteochondral transplant, or to allow retrograde fixation of a graft within two sockets, for example).

As described in more detail below, formation of the recipient socket begins by inserting an outer tube and an inner tube (i.e., a shaft) of the instrument into the joint space, preferably from the outside in, through a small diameter tunnel. A cutting blade is attached to both the outer tube and the inner tube of the instrument. The cutting blade may be provided with a suture passing notch in the blade. Once the shaft undergoes linear movement or linear motion, a mechanism (a pin and slot mechanism, for example) converts the linear movement of the shaft (in relation to the tube) into rotational movement of the cutting blade. The pin and slot mechanism also locks the blade on the outer tube when the blade is in the "flip" position. A socket is created by conducting a drilling operation while the device is pulled in a retrograde manner, as described, for example, in U.S. Patent Application Publ. No. 2008/0306483, the disclosure of which is incorporated by reference in its entirety herewith. Other methods of retrograde drilling known in the art may also be used to create the socket.

Figure 10:
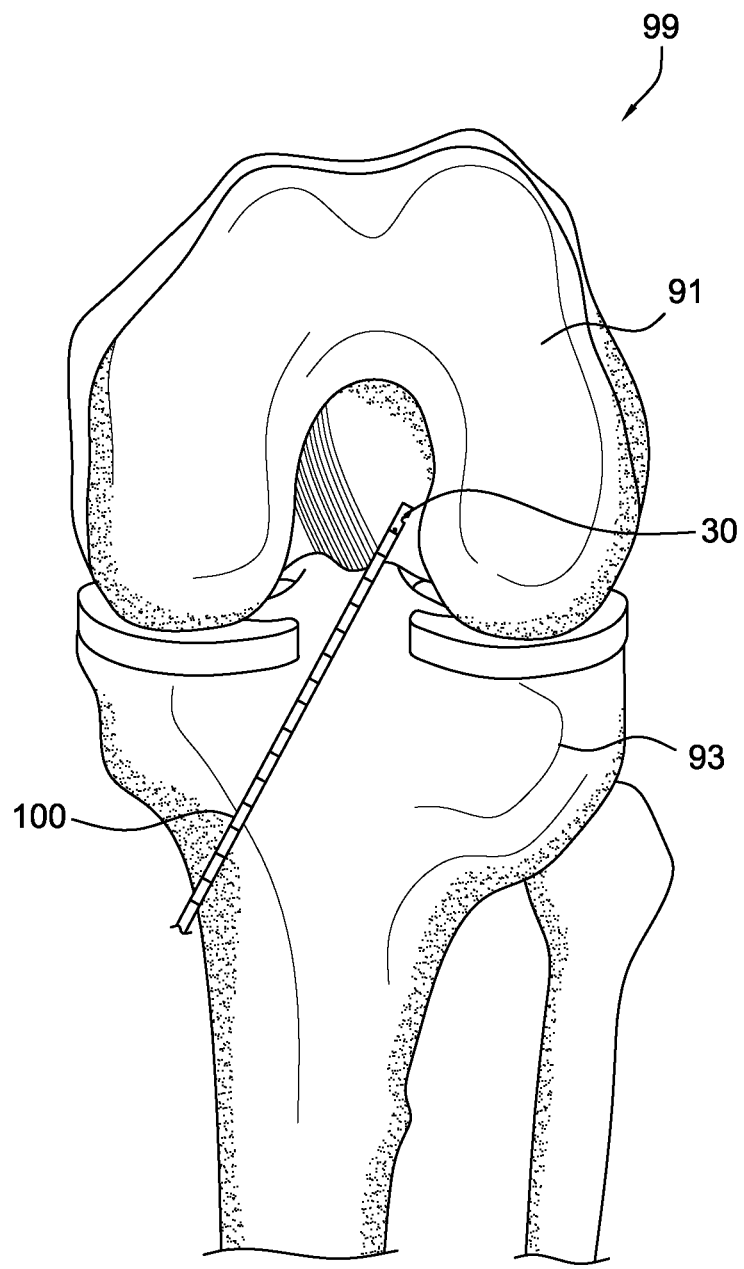
FIG. 10 schematically illustrates the formation of a socket with the flip cutter of the present invention.

Referring now to the drawings, where like elements are designated by like reference numerals, FIGS. 1-9 illustrate various views of flip cutter 100, 200 of the present invention and at various stages of converting linear motion to rotational motion. FIG. 10 illustrates a schematic view of the retrograde flip cutter 100 of FIGS. 1-4 provided in the vicinity of a knee, where ACL reconstruction is conducted according to the present invention. The flip cutter 100, 200 creates a recipient site socket from the inside out, i.e., using a retrograde technique, with minimal incisions of distal cortices and reduced intraarticular bone fragmentation of tunnel rims.

FIGS. 1-4 illustrate a first embodiment of flip cutter 100 of the present invention while FIGS. 5-9 illustrate a second embodiment of flip cutter 200 of the present invention (provided with a push button mechanism for deployment, and also with a suture passing notch in the cutting blade). As illustrated in FIGS. 1-4, flip cutter 100 includes a cannulated elongated outer tube 10 having a distal end 12 and a proximal end (not shown). Distal end 12 is provided (at its most distal part) with a mechanism 15 that is configured to engage a corresponding structure of blade 30 to be attached and securely engaged to the outer tube 10.

Figure 1:
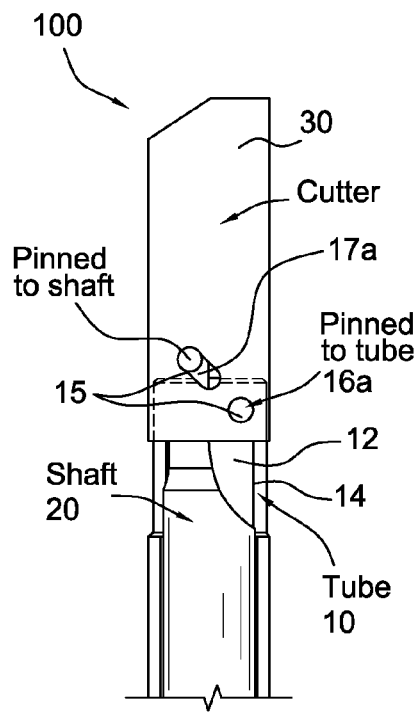
FIG. 1 illustrates a schematic cross-sectional view of a flip cutter according to a first embodiment of the present invention, and with the blade in the "straight" configuration.

The outer tube 10 of the retrograde cutter 100 houses an inner tube or shaft 20 with a diameter smaller than that of the outer tube 10. Blade 30 is provided at distal end 12 of the outer tube 10 and is connected to both the outer tube 10 and the inner shaft 20 by mechanism 15. In an exemplary embodiment, and as shown in FIG. 1, blade 30 is pinned to the outer tube 10 and is also pinned to the shaft 20. Outer tube 10 is provided with a cutout 14 that allows movement of blade 15 within the cutout and relative to the outer tube 10. Blade 30 of the cutter 100 may have a body provided in various shapes and geometries, and may include cutting edges or surfaces also of various configurations.

Figure 2:
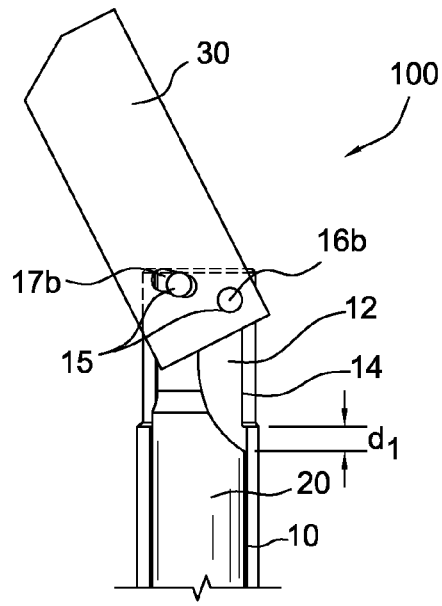
FIGS. 2 and 3 illustrate the flip cutter of FIG. 1, with the blade in sequential "flip" configurations.
Figure 3:
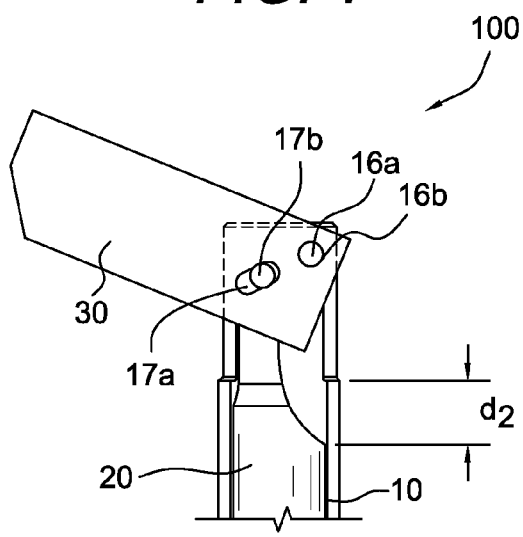

In an exemplary embodiment, mechanism 15 comprises a pin and a slot that allow conversion of the linear movement of the shaft of the instrument into rotational movement of the cutter tip (cutting blade) of the instrument. For example, as shown in FIGS. 1-4, mechanism 15 may include a first pin hole 16a (or first pin slot 16a) with a first pin 16b connecting blade 30 to tube 10, where the first pin hole 16a permits only rotational movement, and a second pin hole 17a (or second pin slot 17a) with a second pin 17b connecting blade 30 to shaft 20, where the second pin hole 17a is a slot permitting rotational and sliding movement of blade 30 relative to the second pin 17b. As shown in FIGS. 2 and 3, when tube 10 is advanced in a linear direction parallel to the longitudinal axis of the flip cutter 100, the first pin pushes one side of the proximal end of blade 30 in the linear direction, while the second pin is permitted to slide in the slot of the second pin hole, thus permitting rotation of blade 30.

In use, blade 30 is attached to both the outer tube 10 and the inner tube 20 by engaging mechanism 15. The outer tube 10 and the inner tube 20, with the blade attached and locked in the "straight" configuration, are inserted into a joint from the distal side, until they are visible in the joint.

Figure 4:
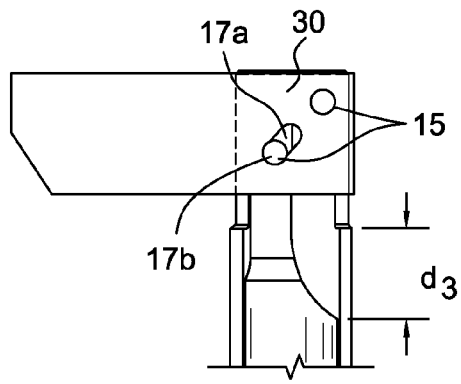
FIG. 4 illustrates the flip cutter of FIG. 1, with the blade in the locked "flip" configuration.
Figure 5:
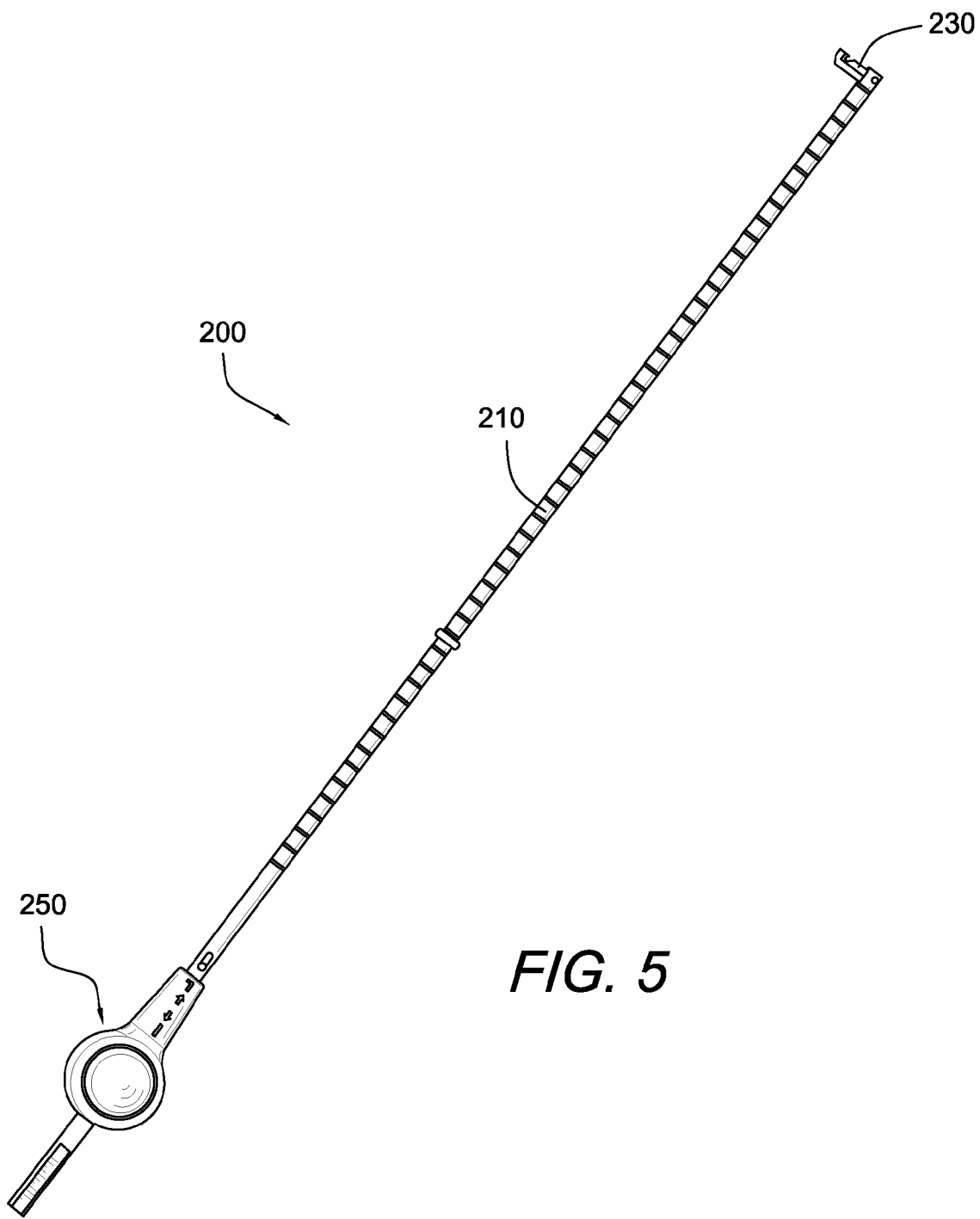
FIG. 5 illustrates a perspective view of a flip cutter according to a second embodiment of the present invention, and with the blade in the "flip" configuration.
Figure 6:
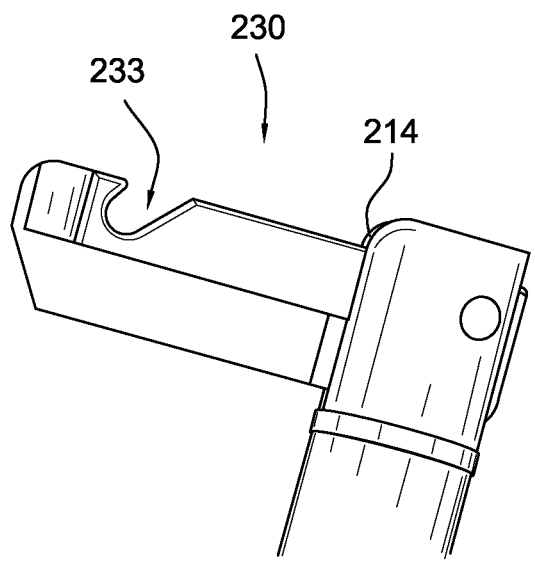
FIG. 6 illustrates a side view of the flip cutter of FIG. 5, with the blade in the locked "flip" configuration.
Figure 7:
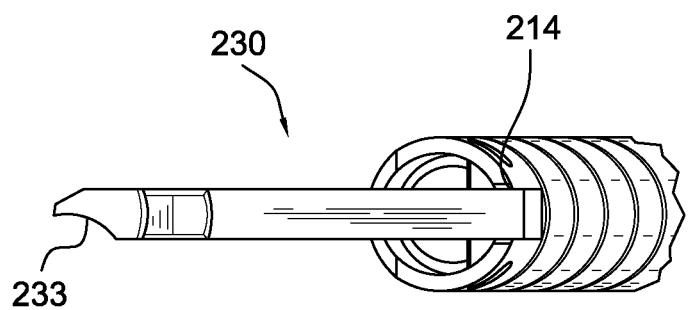
FIG. 7 illustrates a top view of the flip cutter of FIG. 5, with the blade in the locked "flip" configuration.
Figure 8:
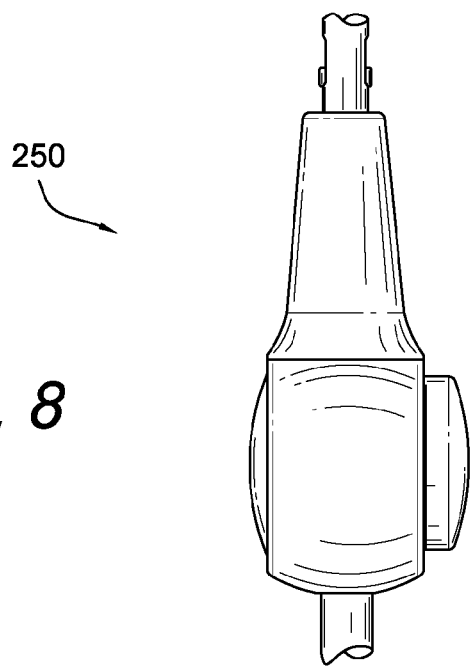
FIGS. 8 and 9 illustrate side views of the push button mechanism of the flip cutter of FIG. 5.
Figure 9:
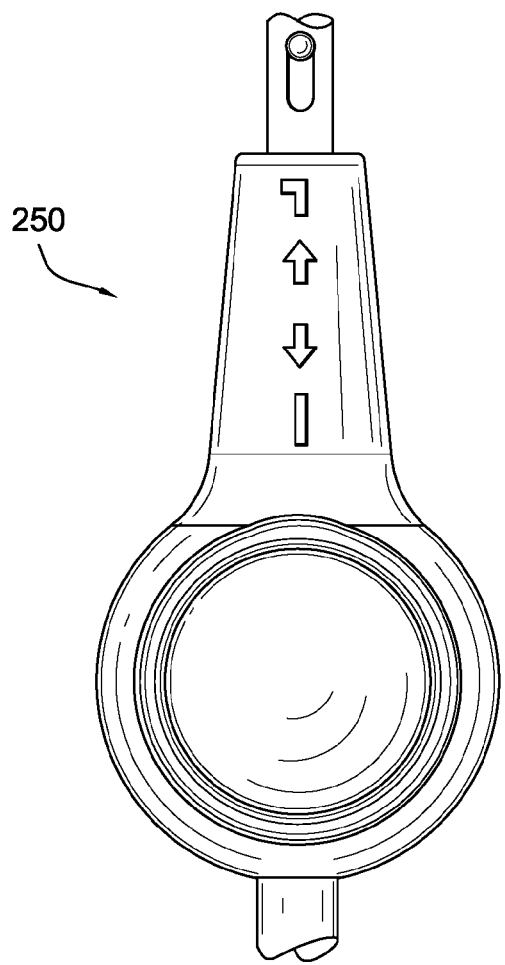

Once the instrument reaches the joint, a linear motion may be carried out so that one of the tubes 10, 20 advances relative to the other of the tubes 10, 20 (for example, the outer tube 10 advances relative to the inner shaft 20) by sequential distances $d_1$ (FIG. 2), $d_2$ (FIG. 3) and $d_3$ (FIG. 4). At the point where outer tube 10 travels distance $d_3$ (FIG. 4) relative to the inner tube 20 (or when the inner tube 20 travels distance $d_3$ relative to the outer tube 10), the blade 30 is in a locked and "flip" position, i.e., about perpendicular to the longitudinal axis of the instrument. In this manner, movement of the outer tube relative to the inner shaft (i.e., while traveling a distance between about 0 to about $d_3$) converts the linear motion of the tube into a rotational motion of blade 30.

Although FIGS. 1-4 illustrate blade 30 being articulated to the second position upon movement of tube 10 in a distal direction, it should be understood that other embodiments could include blade 30 being articulated to the second position upon movement of either shaft 20 or tube 10 in a proximal direction. In addition, although FIGS. 1-4 illustrate outer tube 10 being moved linearly, it should be understood that the articulation of blade 30 to the second position occurs according to relational movement of the outer and inner tubes, and thus other embodiments could include inner tube 20 being moved in a linear (distal or proximal) direction.

Once blade 30 is locked onto cutting instrument 100 (FIG. 4), a cutting or drilling operation, for example, a retrograde drilling step, may be subsequently carried, as known in the art. According to an exemplary embodiment only, the cutter of the present invention may be employed in a retrograde manner to form a recipient socket (at the location of an osteochondral lesion developed on the head of the tibia, for example, or to accommodate retrograde fixation of a graft within two sockets). For example, and as detailed below, FIG. 10 illustrates cutter 100 of FIGS. 1-4 in the vicinity of femur 91 and tibia 93 of knee 99.

FIGS. 5-9 illustrate flip cutter 200 according to another embodiment of the present invention. Flip cutter 200 is similar to the flip cutter 100 of FIGS. 1-4, but differs in that the handle of cutter 200 includes a push button mechanism 250 (illustrated in detail in FIGS. 8 and 9) for deployment of blade 230. Flip cutter 200 also differs from the flip cutter 100 of FIGS. 1-4 in that blade 230 is provided with a suture passing notch 233 (illustrated in more detail in FIGS. 6 and 7). As in the previously-described embodiment, outer tube 210 of the cutter 200 is provided at its most distal end with a cutout 214 that allows blade 230 to pivot from an angle of about zero degrees relative to a longitudinal axis of the tube 210 to an angle of about ninety degrees relative to the longitudinal axis of the tube 210.

Push button mechanism 250 may be configured to advance an inner or outer tube of a body 210 of flip cutter 200 (i.e., similar to shaft 20 and tube 10 of flip cutter 100 in FIGS. 1-4) in a linear direction (for example, a distal direction) to rotate and lock blade 230 in a "flip" position using a mechanism similar to the configuration described above with regard to flip cutter 100. In another exemplary embodiment, push button mechanism 250 may lock cutter 200 and prevent relational movement of the inner and outer tubes until push button mechanism 250 is engaged.

An exemplary method of ACL reconstruction may be performed according to an embodiment of the present invention by employing cutter 100 (FIGS. 1-4) or cutter 200 (FIGS. 5-9) to form at least one of a femoral and tibial socket. For example, with cutter 100 oriented as shown in FIG. 10, a tibial socket or tunnel is formed within tibia 93 in a retrograde manner.

The present invention may be used to form various sockets or tunnels to allow fixation of a graft (for example, a semitendonosus allograft) or to allow replacement of osteochondral cores or implants in a retrograde manner, to obviate inserting harvesters into the joint. For example, cutting instrument 100, 200 of the present invention may be employed for the formation of sockets during an "All-Inside ACL Retro-Construction" for ligament repair, developed by Arthrex, Inc. of Naples, Fla. (and disclosed in U.S. Patent Application Publ. No. 2009/0275950, incorporated by reference above), which comprises, for example, the steps of: (i) drilling at least one of a femoral and tibial tunnel or socket using the cutting instrument 100, 200 of FIGS. 1-9; (ii) providing a graft (soft tissue graft or BTB graft) in the vicinity of the sockets; and (iii) securing the graft within the femoral and tibial tunnels (sockets).

According to yet another embodiment, an exemplary method of ACL retrograde reconstruction of the present invention comprises, for example, the steps of: (i) drilling a femoral socket; (ii) drilling a tibial tunnel or socket using a retrodrill technique employing the cutting instrument 100, 200 of FIGS. 1-9; (iii) providing a graft (soft tissue graft or BTB graft) in the vicinity of the sockets; (iv) securing the graft (soft tissue graft or BTB graft) to a continuous loop/button construct comprising a button with an oblong configuration and provided with an inside eyelet that allows the passage of the continuous loop, preferably a suture loop; (v) passing the graft with the button through the femoral tunnel; (vi) securing the button to the femoral cortex once the button exits the femoral socket; and (vii) securing the graft in the tibial tunnel or socket.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed as new and desired to be protected by Letters Patent of the United States is:

1. A method of retrograde drilling comprising:
    providing a retrograde cutter including an outer tube and an inner tube housed by said outer tube, a blade at distal ends of said outer and inner tubes, the blade being configured to rotate from a first position generally aligned with a longitudinal axis of said retrograde cutter to a second, flip position which is not aligned with said longitudinal axis; and a mechanism connecting said blade to said distal ends of both said outer and inner tubes, wherein said mechanism comprises a pin and a slot that allow conversion of linear movement of the inner tube into rotational movement of the blade to rotate said blade to said second, flip position upon linear movement of the inner tube in relation to the outer tube, the pin sliding in the slot to permit rotation of the blade, wherein the pin and slot mechanism locks the blade on the outer tube when the blade is in the second, flip position;
    inserting said blade into a target area;
    advancing said inner tube in relation to the outer tube in a direction parallel to said longitudinal axis, such that said mechanism articulates said blade from said first position to said second, flip position which is not aligned with said longitudinal axis and wherein the blade is articulated to an angle of about 90 degrees to the longitudinal axis of the retrograde cutter when the blade is in the second, flip position and wherein in the second, flip position, the blade faces a proximal end of the retrograde cutter for retrograde drilling of a socket when the blade is locked in the second, flip position; and
    drilling a socket in a retrograde manner using said blade in said second, flip position.

2. The method of claim 1, further comprising advancing said inner tube in relation to said outer tube until said blade reaches said second position.

3. The method of claim 2, wherein said mechanism comprises a first pin connecting said blade to said outer tube and a second pin connecting said blade to said inner tube, and said blade comprises a first pin hole for connecting said blade to said first pin and a second pin hole for connecting said blade to said second pin,
    said step of advancing further comprising moving said blade rotationally about said first pin and rotationally and slidingly about said second pin such that said blade rotates from said first position to said second position.

4. The method of claim 1, said step of inserting said blade into said target area comprising advancing said retrograde cutter through a cannula in a distal direction such that said blade is located distally beyond a joint.

5. The method of claim 4, said step of drilling further comprising rotating said retrograde cutter while pulling said retrograde cutter in a proximal direction.

6. The method of claim 1, said retrograde cutter further comprising a button mechanism at said proximal end of said inner and outer tubes, wherein said step of advancing said outer tube in relation to said inner tube comprises engaging said button to advance one of said inner and outer tubes in relation to the other of said inner and outer tubes.

7. The method of claim 1, wherein said blade comprises a notch for holding a suture material, said step of inserting said blade into a target area further comprising passing a suture held in said notch into said target area.

* * * * *